(12) United States Patent
Udupa et al.

(10) Patent No.: US 10,006,950 B2
(45) Date of Patent: Jun. 26, 2018

(54) IMPEDANCE MEASUREMENT CIRCUIT

(71) Applicant: Texas Instruments Incorporated, Dallas, TX (US)

(72) Inventors: Anand Hariraj Udupa, Bangalore (IN); Jagannathan Venkataraman, Bangalore (IN); Hussam Ahmed P, Calicut (IN); Sandeep Kesrimal Oswal, Bangalore (IN)

(73) Assignee: Texas Instruments Incorporated, Dallas, TX (US)

( * ) Notice: Subject to any disclaimer, the term of this patent is extended or adjusted under 35 U.S.C. 154(b) by 351 days.

(21) Appl. No.: 14/694,500

(22) Filed: Apr. 23, 2015

(65) Prior Publication Data

US 2015/0305648 A1 Oct. 29, 2015

(30) Foreign Application Priority Data

Apr. 24, 2014 (IN) .......................... 2086/CHE/2014

(51) Int. Cl.
*G01R 27/08* (2006.01)
*A61B 5/053* (2006.01)

(52) U.S. Cl.
CPC ............. *G01R 27/08* (2013.01); *A61B 5/053* (2013.01)

(58) Field of Classification Search
CPC ........ G01R 27/08; A61B 5/0537; A61B 5/053
See application file for complete search history.

(56) References Cited

U.S. PATENT DOCUMENTS

| | | | |
|---|---|---|---|
| 3,851,641 A | 12/1974 | Toole et al. | |
| 3,871,359 A | 3/1975 | Pacela | |
| 4,459,995 A | 7/1984 | Conners et al. | |
| 5,187,096 A | 2/1993 | Giaever et al. | |
| 7,443,175 B2 | 10/2008 | Podhajsky et al. | |
| 7,941,210 B2 | 5/2011 | Matthiessen et al. | |
| 2002/0079910 A1 | 6/2002 | Fukuda | |
| 2008/0012582 A1 | 1/2008 | Jang et al. | |
| 2008/0036475 A1 | 2/2008 | Waki | |

(Continued)

OTHER PUBLICATIONS

AFE4300, Low-Cost, Integrated Analog Front-End for Weight-Scale and Body Composition Measurement, available at http://www.ti.com/lit/ds/symlink/afe4300.pdf, 2013.*

(Continued)

*Primary Examiner* — Daniel Miller
(74) *Attorney, Agent, or Firm* — William B. Kempler; Charles A. Brill; Frank D. Cimino

(57) ABSTRACT

The disclosure provides a circuit for impedance measurement. The circuit includes an excitation source that generates an excitation signal. A switched resistor network is coupled to the excitation source, and generates an output signal in response to the excitation signal. A sense circuit is coupled to the switched resistor network, and generates a sense signal in response to the output signal. A comparator is coupled to the sense circuit, and generates a clock signal in response to the sense signal. A mixer is coupled to the sense circuit, and multiplies the sense signal and the clock signal to generate a rectified signal. A low pass filter is coupled to the mixer and filters the rectified signal to generate an averaged signal. A processor is coupled to the low pass filter and measures a body impedance from the averaged signal.

22 Claims, 6 Drawing Sheets

(56) References Cited

U.S. PATENT DOCUMENTS

2008/0275361 A1* 11/2008 Loriga ................ A61B 5/0535
                                                          600/547
2010/0004548 A1   1/2010  Rytky
2010/0016809 A1   1/2010  Gröber et al.
2010/0102834 A1   4/2010  Shyu
2011/0169511 A1   7/2011  Nordin et al.
2015/0293045 A1  10/2015  Udupa et al.

OTHER PUBLICATIONS

AFE4300 Development Guide, User's Guide, available at http://www.ti.com/lit/ug/sbau201/sbau201.pdf, 2012.*
U.S. Appl. No. 15/465,484, filed Mar. 21, 2017, 30 pages.

* cited by examiner

IMPEDANCE MEASUREMENT CIRCUIT

CROSS REFERENCES TO RELATED APPLICATIONS

This application claims priority from India provisional patent application No. 2086/CHE/2014 filed on Apr. 24, 2014 which is hereby incorporated by reference in its entirety.

TECHNICAL FIELD

The present disclosure is generally related to an impedance measurement circuit, and more particularly to measuring body impedance using the impedance measurement circuit.

BACKGROUND

In biomedical engineering, bio-impedance is the response of a living organism to externally applied electric current. Bio-impedance or body impedance is a measure of the opposition to the flow of that electric current through the tissues, the opposite of the electrical conductivity. The measurement of the body impedance of humans and animals has proved useful as a non-invasive method for measuring blood flow, body fat, BMI (body mass index) and body composition.

One method of measuring the body impedance uses electrodes. A fixed excitation current (either AC or DC) is injected in a human body through a pair of excitation electrodes. A pair of sense electrodes is coupled to the human body. A sense circuit measures a voltage difference across the sense electrodes. The voltage difference corresponds to the impedance of the human body.

An impedance associated with each electrode of the pair of excitation electrodes and the pair of sense electrodes effects the accuracy of the measured body impedance. Traditional devices does not take into consideration the high range of impedance associated with the electrodes, because these devices provide large electrodes which allow a large area of contact between the electrode and the human body. However, modern consumer devices like cell phones need to take into consideration the impedance associated with the electrodes or mismatched impedances between the electrodes.

In a calibration method, the body impedance is calibrated with respect to known resistors that are measured using the sense circuit. However, the calibration method suffers from inaccuracies owing to the impedance associated with the electrodes. The impedance associated with the electrodes is present when the body impedance is measured. However, the impedance associated with the electrodes is not taken into consideration when the known resistors are measured. Thus, this leads to inaccuracies in the measurement of the body impedance.

SUMMARY

According to an aspect of the disclosure, a circuit is disclosed. The circuit includes an excitation source that generates an excitation signal. A switched resistor network is coupled to the excitation source, and generates an output signal in response to the excitation signal. A sense circuit is coupled to the switched resistor network, and generates a sense signal in response to the output signal. A comparator is coupled to the sense circuit, and generates a clock signal in response to the sense signal. A mixer is coupled to the sense circuit, and multiplies the sense signal and the clock signal to generate a rectified signal. A low pass filter is coupled to the mixer and filters the rectified signal to generate an averaged signal. A processor is coupled to the low pass filter and measures a body impedance from the averaged signal.

BRIEF DESCRIPTION OF THE VIEWS OF DRAWINGS

DETAILED DESCRIPTION OF THE EMBODIMENTS

Figure 1:
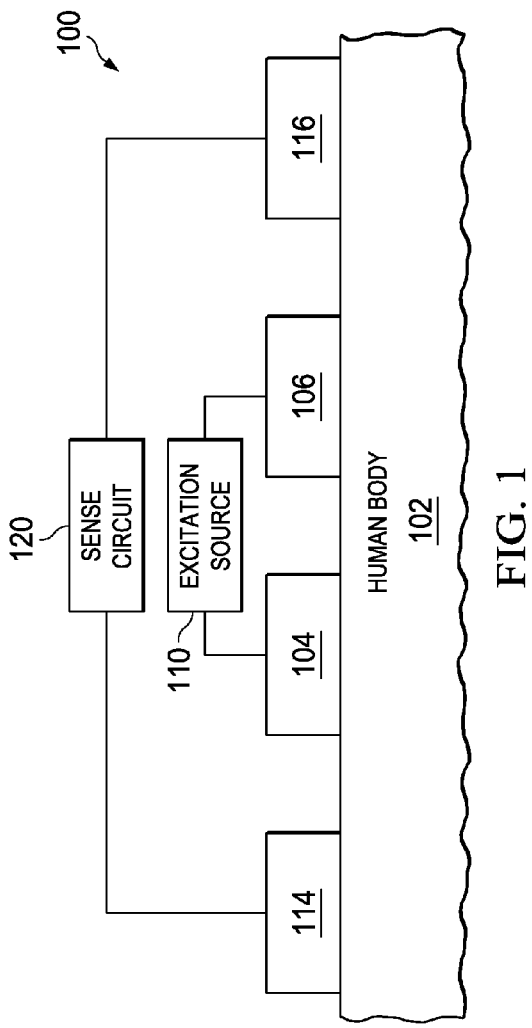
FIG. 1 is a block diagram of an impedance measurement circuit, in which various embodiments can be implemented.

FIG. 1 illustrates a block diagram of an impedance measurement circuit 100, in which various embodiments can be implemented. The impedance measurement circuit 100 is coupled to a human body 102. The impedance measurement circuit 100 includes an excitation source 110. The excitation source 110 is coupled between a pair of excitation electrodes. The pair of excitation electrodes includes a first excitation electrode 104 and a second excitation electrode 106. The first excitation electrode 104 and the second excitation electrode 106 are coupled to the human body 102. A first sense electrode 114 and a second sense electrode 116 are also coupled to the human body 102. A sense circuit 120 is coupled between the first sense electrode 114 and the second sense electrode 116.

An operation of the impedance measurement circuit 100 illustrated in FIG. 1 is explained now. The excitation source 110 generates an AC or a DC signal. In one example, the excitation source 110 generates a high frequency AC current which is injected in the human body 102 through the pair of excitation electrodes 104 and 106. The AC current causes a voltage difference between the first sense electrode 114 and the second sense electrode 116. The sense circuit 120 measures this voltage difference. This voltage difference is related to the resistivity of the human body 102 between the first sense electrode 114 and the second sense electrode 116.

An impedance of the human body 102 is defined as the ratio of the voltage difference between the pair of sense electrodes 114 and 116 and the AC current that is injected in the human body 102.

Figure 2:
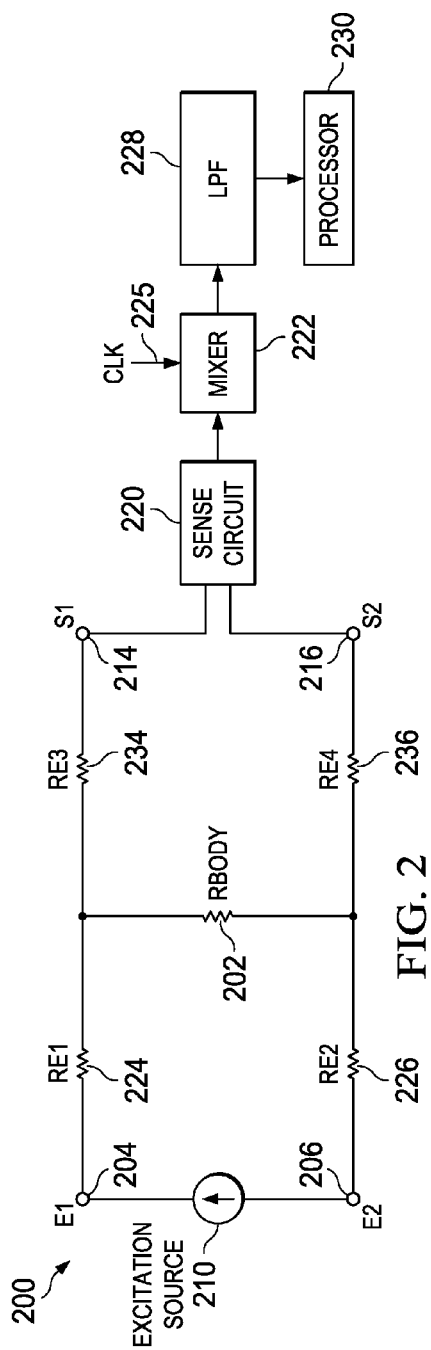
FIG. 2 is a schematic of an impedance measurement circuit.

FIG. 2 is a schematic of an impedance measurement circuit 200. The impedance measurement circuit 200 is a schematic of impedance measurement circuit 100, illustrated in FIG. 1. The impedance measurement circuit 200 includes an excitation source 210 similar to the excitation source 110.

The excitation source 210 is coupled between a first excitation terminal E1 204 and a second excitation terminal E2 206. The first excitation terminal E1 204 corresponds to the first excitation electrode 104, and the second excitation terminal E2 206 corresponds to the second excitation electrode 106. An impedance associated with the first excitation electrode 104 is represented by a first input electrode impedance RE1 224, and an impedance associated with the second excitation electrode 106 is represented by a second input electrode impedance RE2 226.

A body impedance RBODY 202 represents an impedance associated with the human body, for example human body 102 represented in FIG. 1. A sense circuit 220 is coupled between a first sense terminal S1 214 and a second sense terminal S2 216. The first sense terminal S1 214 corresponds to the first sense electrode 114, and the second sense terminal S2 216 corresponds to the second sense electrode 116.

An impedance associated with the first sense electrode 114 is represented as a first output electrode impedance RE3 234, and an impedance associated with the second sense electrode 116 is represented as a second output electrode impedance RE4 236. The first output electrode impedance RE3 234 is coupled to the first input electrode impedance RE1 224, the body impedance RBODY 202 and the first sense terminal S1 214.

The second output electrode impedance RE4 236 is coupled to the second input electrode impedance RE2 226, the body impedance RBODY 202 and the second sense terminal S2 216. In addition, to the elements mentioned in FIG. 1, the impedance measurement circuit 200 includes a mixer 222, a low pass filter (LPF) 228 and a processor 230. The mixer 222 is coupled to the sense circuit 220, and the LPF 228 is coupled to the mixer 222. The mixer 222 receives a clock signal CLK 225. The processor 230 is coupled to the LPF 228.

The operation of the impedance measurement circuit 200 illustrated in FIG. 2 is explained now. The excitation source 210 generates and AC or a DC signal. In one example, the excitation source 210 generates a high frequency AC current. When the excitation source 210 generates an AC signal, it is clocked by the clock signal CLK 225. The AC current is injected in the human body through the pair of excitation electrodes. The AC current traverses from the first excitation terminal E1 204 to the second excitation terminal E2 206 through the body impedance RBODY 202.

A voltage difference is created between the first sense terminal S1 214 and the second sense terminal S2 216. The sense circuit 220 measures this voltage difference, and generates a sense signal. The mixer 222 multiplies the clock signal CLK 225 and the sense signal to generate a rectified signal. The LPF 228 filters the rectified signal received from the mixer 222, and generates an averaged signal. The processor 230 measures the body impedance RBODY 202 from the averaged signal.

The body impedance RBODY 202 is a resistivity of the human body 102 between the first sense terminal S1 214 and the second sense terminal S2 216. The combination of the mixer 222 and the LPF 228 provides full wave rectification of the sense signal (which is an AC signal) to generate the averaged signal (which is a DC signal) for the body impedance RBODY 202 measurement. The full wave rectification is achieved by multiplication of the sense signal and the clock signal CLK 225.

Ideally, since the excitation source 210 and mixer 222 are clocked by the clock signal CLK 225, the sense signal is assumed to be in-phase with the clock signal CLK 225. However, in real world scenario, the clock signal CLK 225 and the sense signal are out-of-phase. This is because of the phase shifts introduced in the excitation signal by the body impedance RBODY 202, and parasitic capacitances of the excitation and sense electrodes. This leads to inaccuracies in the measurement of the body impedance RBODY 202.

Figure 3:
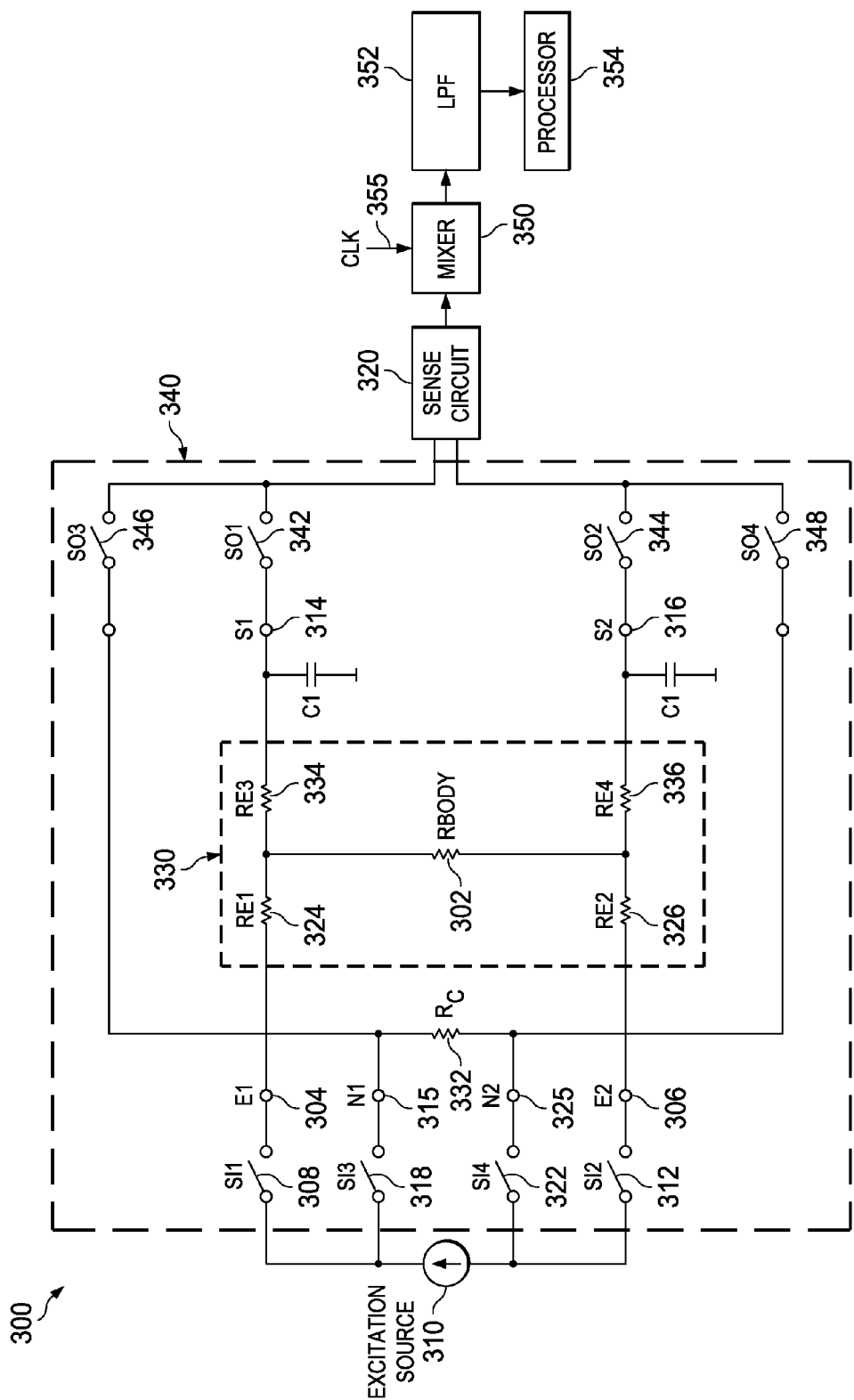
FIG. 3 is a schematic of a circuit.

FIG. 3 is a schematic of a circuit 300. The circuit 300, in one example, in an impedance measurement circuit. The circuit 300 includes an excitation source 310, a switched resistor network 340, a sense circuit 320, a mixer 350, a low pass filter (LPF) 352 and a processor 354. The switched resistor network 340 is coupled to the excitation source 310. The sense circuit 320 is coupled to the switched resistor network 340.

The mixer 350 is coupled to the sense circuit 320 and the LPF 352. The mixer 350 receives a clock signal CLK 355. The processor 354 is coupled to the LPF 352. The switched resistor network 340 includes a first set of input switches, a calibration resistor Rc 332 and an impedance network 330. The first set of input switches includes a first input switch SI1 308, and a second input switch SI2 312. The switched resistor network 340 also includes a first set of output switches and a second set of output switches. The first set of output switches includes a first output switch SO1 342 and a second output switch SO2 344.

The second set of output switches includes a third output switch SO3 346 and a fourth output switch SO4 348. The excitation source 310 is coupled between the first input switch SI1 308 and the second input switch SI2 312. The first set of output switches (SO1, SO2) are coupled to the sense circuit 320. The impedance network 330 is coupled between the first set of input switches and the first set of output switches.

The switched resistor network 340 also includes a second set of input switches that includes a third input switch SI3 318 and a fourth input switch SI4 322. The second set of input switches is coupled in parallel to the first set of input switches. The excitation source 310 is coupled between the second set of input switches i.e. the excitation source is coupled between the third input switch SI3 318 and the fourth input switch SI4 322. The third input switch SI3 318 is coupled between the excitation source 310 and a first node N1 315. The fourth input switch SI4 322 is coupled between the excitation source 310 and a second node N2 325.

The calibration resistor Rc 332 is coupled between the first node N1 315 and the second node N2 325. One end of the third output switch SO3 346 is coupled to the first node N1 315 and the calibration resistor Rc 332, while the other end is coupled to the sense circuit 320. One end of the fourth output switch SO4 348 is coupled to the second node N2 325 and the calibration resistor Rc 332, while the other end is coupled to the sense circuit 320.

The impedance network 330 includes a body impedance RBODY 302 and a plurality of electrode impedances. The plurality of electrode impedance includes a first input electrode impedance RE1 324, a second input electrode impedance RE2 326, a first output electrode impedance RE3 334 and a second output electrode impedance RE4 336. The body impedance RBODY 302 is coupled between the first input electrode impedance RE1 324 and the second input electrode impedance RE2 312.

The first input electrode impedance RE1 324 is coupled to a first excitation terminal E1 304. The second input electrode impedance RE2 326 is coupled to a second excitation terminal E2 306. The body impedance RBODY 302 is coupled between the first input electrode impedance RE1 334 and the second input electrode impedance RE2 326. The first output electrode impedance RE3 334 is coupled to a first sense terminal S1 314, and the second output electrode impedance RE4 336 is coupled to a second sense terminal S2 316.

The first excitation terminal E1 304 corresponds to a first excitation electrode (similar to the first excitation electrode 104), and the second excitation terminal E2 306 corresponds to a second excitation electrode (similar to the second excitation electrode 106). An impedance associated with the first excitation electrode is represented by the first input electrode impedance RE1 324, and an impedance associated with the second excitation electrode is represented by a second input electrode impedance RE2 326. An impedance associated with the human body 102 is represented as a body impedance RBODY 302.

The first sense terminal S1 314 corresponds to a first sense electrode (similar to the first sense electrode 114), and the second sense terminal S2 316 corresponds to a second sense electrode (similar to the second sense electrode 116). An impedance associated with the first sense electrode is represented as the first output electrode impedance RE3 334, and an impedance associated with the second sense electrode is represented as the second output electrode impedance RE4 336. The first sense electrode has an associated first parasitic capacitance C1, and the second sense electrode has an associated second parasitic capacitance C2.

The first input switch SI1 308 is coupled between the excitation source 310 and the first excitation terminal E1 304. The second input switch SI2 312 is coupled between the excitation source 310 and the second excitation terminal E2 306. The first output switch SO1 342 is coupled between the first sense terminal S1 314 and the sense circuit 320. The second output switch SO2 344 is coupled between the second sense terminal S2 316 and the sense circuit 320.

The operation of the circuit 300 illustrated in FIG. 3 is explained now. The excitation source 310 generates an excitation signal. In one example, the excitation signal is a high frequency AC signal. The excitation source 310 is clocked by the clock signal CLK 355. The processor 354 measures the body impedance RBODY 302 when the first input switch SI1 308, the second input switch SI2 312, the first output switch SO1 342 and the second output switch SO2 344 are closed.

The AC signal is injected in the human body through the pair of excitation electrodes. The AC signal traverses from the first excitation terminal E1 304 to the second excitation terminal E2 306 through the body impedance RBODY 302. A voltage difference is created between the first sense terminal S1 314 and the second sense terminal S2 316.

The switched resistor network 340 generates an output signal in response to the excitation signal received from the excitation source 310. The output signal is proportional to the voltage difference created between the first sense terminal S1 314 and the second sense terminal S2 316. The sense circuit 320 generates a sense signal in response to the output signal. The mixer 350 multiplies the clock signal CLK 355 and the sense signal to generate a rectified signal. The LPF 352 filters the rectified signal received from the mixer 350, and generates an averaged signal. The processor 354 measures the body impedance RBODY 302 from the averaged signal.

The circuit 300 uses the calibration resistor Rc 332 to calibrate for an offset associated with the circuit 300. A resistance of the calibration resistor Rc 332 is known to a user. The processor measures the resistance of the calibration resistor Rc 332 when the third input switch SI3 318, the fourth input switch SI4 322, the third output switch SO3 346, and the fourth output switch SO4 348 are closed.

The AC signal generated by the excitation source 310 traverses from the first node N1 315 to the second node N2 325 through the calibration resistor Rc 332. A voltage difference is created between the first node N1 315 and the second node N2 325. An output signal generated by the switched resistor network 340 is proportional to this voltage difference. The output signal is processed in the circuit 300 for measurement of the calibration resistor Rc 332. The processing of the output signal is in a similar manner as discussed with respect to the measurement of the body impedance RBODY 302. A rectified signal generated during measurement of the calibration resistor Rc 332 is used as a reference to calibration the body impedance RBODY 302.

Since, a resistance of the calibration resistor Rc 332 is known beforehand, the measured resistance of the calibration resistor Rc 332 provides an offset associated with the circuit 300. The offset associated with the circuit 300 is subtracted from the measured body impedance RBODY 302 to obtain an accurate value to the body impedance RBODY 302.

However, a voltage swing across the excitation source 310 while traversing from the first excitation terminal E1 304 to the second excitation terminal E2 306 is different from a voltage swing across the excitation source 310 while traversing from the first node N1 315 to the second node N2 325. This difference is caused by the first input electrode impedance RE1 324 and the second input electrode impedance RE2 326.

This difference in voltage swings causes excitation signal (AC signal or AC current) of different magnitude to be generated by the excitation source 310 when the sense circuit 320 measure the body impedance RBODY 302 and the resistance of calibration resistor Rc 332.

Thus, the excitation signal generated by the excitation source 310 has different magnitudes when the processor measures the body impedance RBODY 302 and the resistance of the calibration resistor Rc 332. This leads to inaccuracies in measurement of the offset associated with the circuit 300.

The combination of the mixer 350 and the LPF 352 provides full wave rectification of the sense signal (which is an AC signal) to generate the averaged signal (which is a DC signal) for the body impedance RBODY 302 measurement. The full wave rectification is achieved by multiplication of the sense signal and the clock signal CLK 355.

Ideally, since the excitation source 310 and mixer 350 are clocked by the clock signal CLK 225, the sense signal is assumed to be in-phase with the clock signal CLK 355. However, in real world scenario, the clock signal CLK 355 and the sense signal are out-of-phase.

This is because of the phase shifts introduced in the excitation signal by the body impedance RBODY 302, and parasitic capacitances of the excitation and sense electrodes. In addition, some of the phase shifts are absent when measuring the resistance of the calibration resistor Rc 332. This leads to inaccuracies in the measurement of the body impedance RBODY 302.

Figure 4:
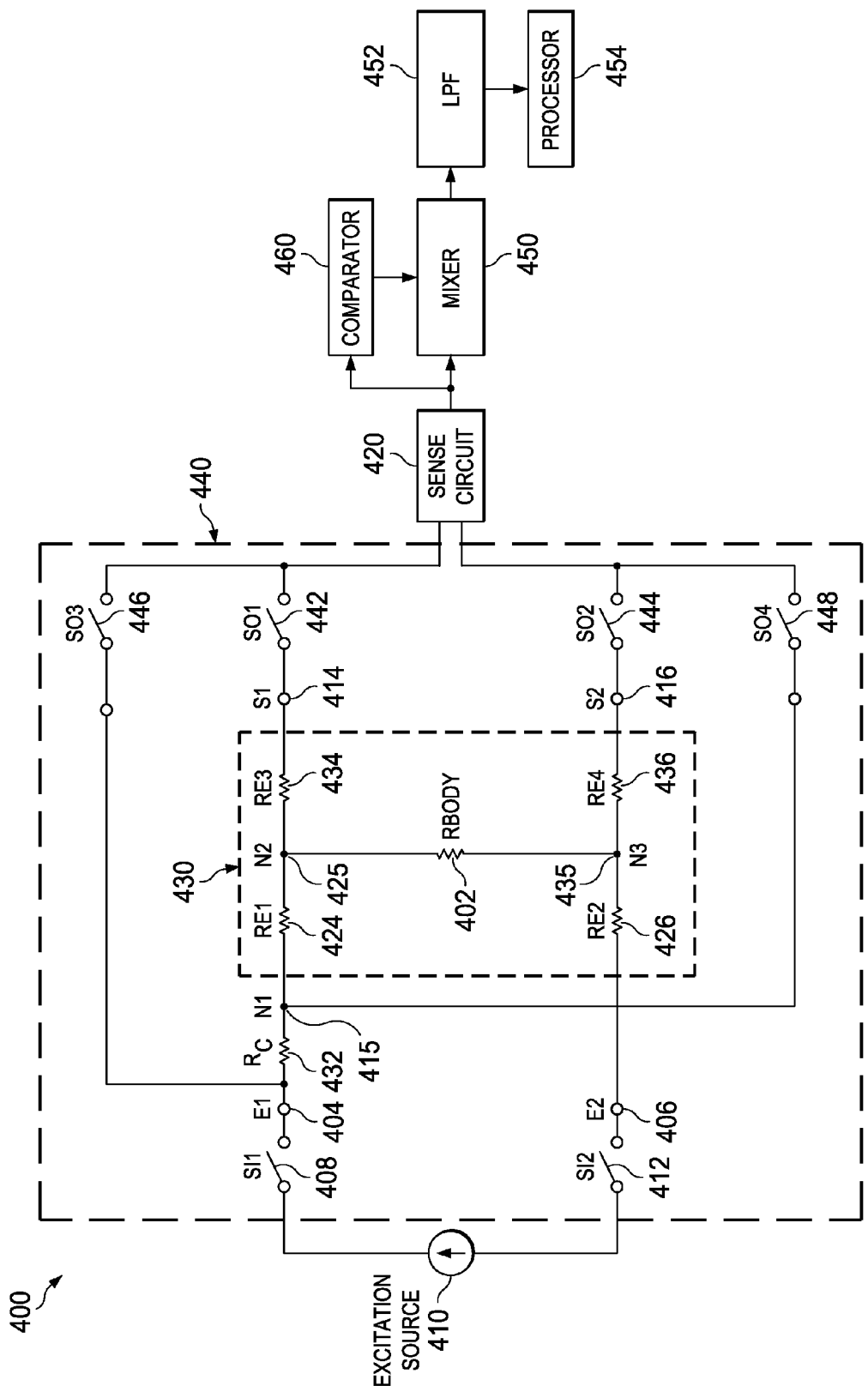
FIG. 4 is a schematic of a circuit, according to an embodiment.

FIG. 4 is a schematic of a circuit 400, according to an embodiment. The circuit 400, in one example, in an impedance measurement circuit. The circuit 400 includes an excitation source 410, a switched resistor network 440, a sense circuit 420, a mixer 450, a comparator 460, a low pass filter (LPF) 452 and a processor 454. The switched resistor network 440 is coupled to the excitation source 410. The sense circuit 420 is coupled to the switched resistor network 440.

The mixer 450 is coupled to the sense circuit 420 and the LPF 452. The comparator 460 is coupled to the sense circuit 420 and the mixer 450. The processor 454 is coupled to the LPF 452. The switched resistor network 440 includes a first set of input switches, a calibration resistor Rc 432 and an impedance network 430. The first set of input switches includes a first input switch SI1 408, and a second input switch SI2 412. The excitation source 410 is coupled between the first input switch SI1 408 and the second input switch SI2 412.

The switched resistor network 440 also includes a first set of output switches and a second set of output switches. The first set of output switches includes a first output switch SO1 442 and a second output switch SO2 444. The second set of output switches includes a third output switch SO3 446 and a fourth output switch SO4 448. The first set of output switches (SO1, SO2) are coupled to the sense circuit 420. The impedance network 430 is coupled between the first set of input switches and the first set of output switches.

The calibration resistor Rc 432 is coupled to the first input switch SI1 408 at a first excitation terminal E1 404. The second set of output switches (SO3, SO4) are coupled across the calibration resistor Rc 432, and are also coupled to the sense circuit 420.

The impedance network 430 includes a body impedance RBODY 402 and a plurality of electrode impedances. The plurality of electrode impedance includes a first input electrode impedance RE1 424, a second input electrode impedance RE2 426, a first output electrode impedance RE3 434 and a second output electrode impedance RE4 436. The body impedance RBODY 402 is coupled between the first input electrode impedance RE1 424 and the second input electrode impedance RE2 412.

The first input electrode impedance RE1 424 is coupled to the first excitation terminal E1 404. The second input electrode impedance RE2 426 is coupled to a second excitation terminal E2 406. The body impedance RBODY 402 is coupled between the first input electrode impedance RE1 344 and the second input electrode impedance RE2 426. The first output electrode impedance RE3 434 is coupled to a first sense terminal S1 414, and the second output electrode impedance RE4 436 is coupled to a second sense terminal S2 416.

The first excitation terminal E1 404 corresponds to a first excitation electrode (similar to the first excitation electrode 104), and the second excitation terminal E2 406 corresponds to a second excitation electrode (similar to the second excitation electrode 106). An impedance associated with the first excitation electrode is represented by the first input electrode impedance RE1 424, and an impedance associated with the second excitation electrode is represented by a second input electrode impedance RE2 426. An impedance associated with the human body 102 is represented as a body impedance RBODY 402.

The first sense terminal S1 414 corresponds to a first sense electrode (similar to the first sense electrode 114), and the second sense terminal S2 416 corresponds to a second sense electrode (similar to the second sense electrode 116). An impedance associated with the first sense electrode is represented as the first output electrode impedance RE3 434, and an impedance associated with the second sense electrode is represented as the second output electrode impedance RE4 436.

The first input switch SI1 408 is coupled between the excitation source 410 and the first excitation terminal E1 404. The second input switch SI2 412 is coupled between the excitation source 410 and the second excitation terminal E2 406. The first output switch SO1 442 is coupled between the first sense terminal S1 414 and the sense circuit 420. The second output switch SO2 444 is coupled between the second sense terminal S2 416 and the sense circuit 420.

The first input electrode impedance RE1 424 is coupled to the calibration resistor Rc 432 at a first common node N1 415. The first input electrode impedance RE1 424, the body impedance RBODY 402 and the first output electrode impedance RE3 434 are coupled to form a second common node N2 425. The second input electrode impedance RE2 426, the body impedance RBODY 402 and the second output electrode impedance RE4 426 are coupled to form a third common node N3 435.

The third output switch SO3 446 is coupled between the first excitation terminal E1 404 and the sense circuit 420. The fourth output switch SO4 448 is coupled between the first common node N1 415 and the sense circuit 420.

In one version, the circuit 400 is part of a medical diagnostic device. In another version, the circuit 400 is integrated in a consumer electronic device such as, but not limited to, a mobile, a PDA (personal digital assistant), and a smartphone. In yet another version, the circuit 400 is part of a device used in industrial application. The circuit 400 may include one or more additional components known to those skilled in the relevant art and are not discussed here for simplicity of the description.

The operation of the circuit 400 illustrated in FIG. 4 is explained now. The excitation source 410 generates an excitation signal. In one example, the excitation signal is high frequency AC signal. The excitation source 410 is clocked by a clock signal CLK. The processor 454 measures the body impedance RBODY 402 when the first input switch SI1 408, the second input switch SI2 412, the first output switch SO1 442 and the second output switch SO2 444 are closed.

The AC signal is injected in the human body through the pair of excitation electrodes. The AC signal traverses from the first excitation terminal E1 404 to the second excitation terminal E2 406 through the body impedance RBODY 402. A voltage difference is created between the first sense terminal S1 414 and the second sense terminal S2 416.

The switched resistor network 440 generates an output signal in response to the excitation signal received from the excitation source 410. The output signal is proportional to the voltage difference created between the first sense terminal S1 414 and the second sense terminal S2 416. The sense circuit 420 generates a sense signal in response to the output signal. The comparator 460 receives the output signal from the sense circuit 420, and generates a clock signal.

The mixer 450 multiplies the clock signal received from the comparator 460 and the sense signal to generate a rectified signal. In one version, the comparator 460 is a zero crossing detector. A time period of the clock signal generated by the comparator 460 is equal to a time period of the excitation signal generated by the excitation source 410. In one version, a phase of the clock signal is equal to a phase of the excitation signal. Deriving the clock signal from the sense signal using the comparator 460 (or a zero crossing detector) eliminates a phase shift between the clock signal and the sense signal.

The LPF 452 filters the rectified signal received from the mixer 450, and generates an averaged signal. The processor 454 measures the body impedance RBODY 402 from the averaged signal.

The circuit 400 uses the calibration resistor Rc 442 to compensate for an offset associated with the circuit 400. A resistance of the calibration resistor Rc 442 is known to a user. The processor measures the resistance of the calibration resistor Rc 442 when the first input switch SI1 408, the second input switch SI2 412, the third output switch SO3 446, and the fourth output switch SO4 448 are closed.

The AC signal generated by the excitation source 410 traverses through the calibration resistor Rc 442. A voltage difference is created between the first excitation terminal E1 404 and the first node N1 415. An output signal generated by the switched resistor network 440 is proportional to this voltage difference. The output signal is processed in the circuit 400 for measurement of the calibration resistor Rc 432. The processing of the output signal is in a similar manner as discussed with respect to the measurement of body impedance RBODY 402.

Since, a resistance of the calibration resistor Rc 432 is known beforehand, the measured resistance of the calibration resistor Rc 432 provides an offset associated with the circuit 400. The offset associated with the circuit 400 is subtracted from the measured body impedance RBODY 402 to obtain an accurate value to the body impedance RBODY 402.

In addition, a voltage swing across the excitation source 410 while traversing from the first excitation terminal E1 404 to the second excitation terminal E2 406 is similar to a voltage swing across the excitation source 410 while traversing from the first excitation terminal E1 404 to the first node N1 415. This means that the voltage swing across the excitation source 410 is same when measuring the body impedance RBODY 402 and when measuring the resistance of the calibration resistor Rc 432. Thus, the excitation signal generated by the excitation source 410 has equal magnitudes when the processor measures the body impedance RBODY 402 and the resistance of the calibration resistor Rc 432. In one version, a voltage generated as the excitation signal is equal during measurement of body impedance RBODY 402 and during measurement of the calibration resistor Rc 432. This leads to accurate measurement of the offset associated with the circuit 400.

The combination of the mixer 450 and the LPF 452 provides full wave rectification of the sense signal (which is an AC signal) to generate the averaged signal (which is a DC signal) for the body impedance RBODY 402 measurement. The full wave rectification is achieved by multiplication of the sense signal and the clock signal generated by the comparator 460.

Since, the comparator 460 generates the clock signal from the sense signal, the clock signal and the sense signal are in-phase. Also, generating the clock signal from the sense signal eliminates errors due to additional phase shifts in the path of body impedance RBODY 402 with respect to the calibration resistor Rc 432. This leads to accurate measurement of the body impedance RBODY 402.

Figure 5:
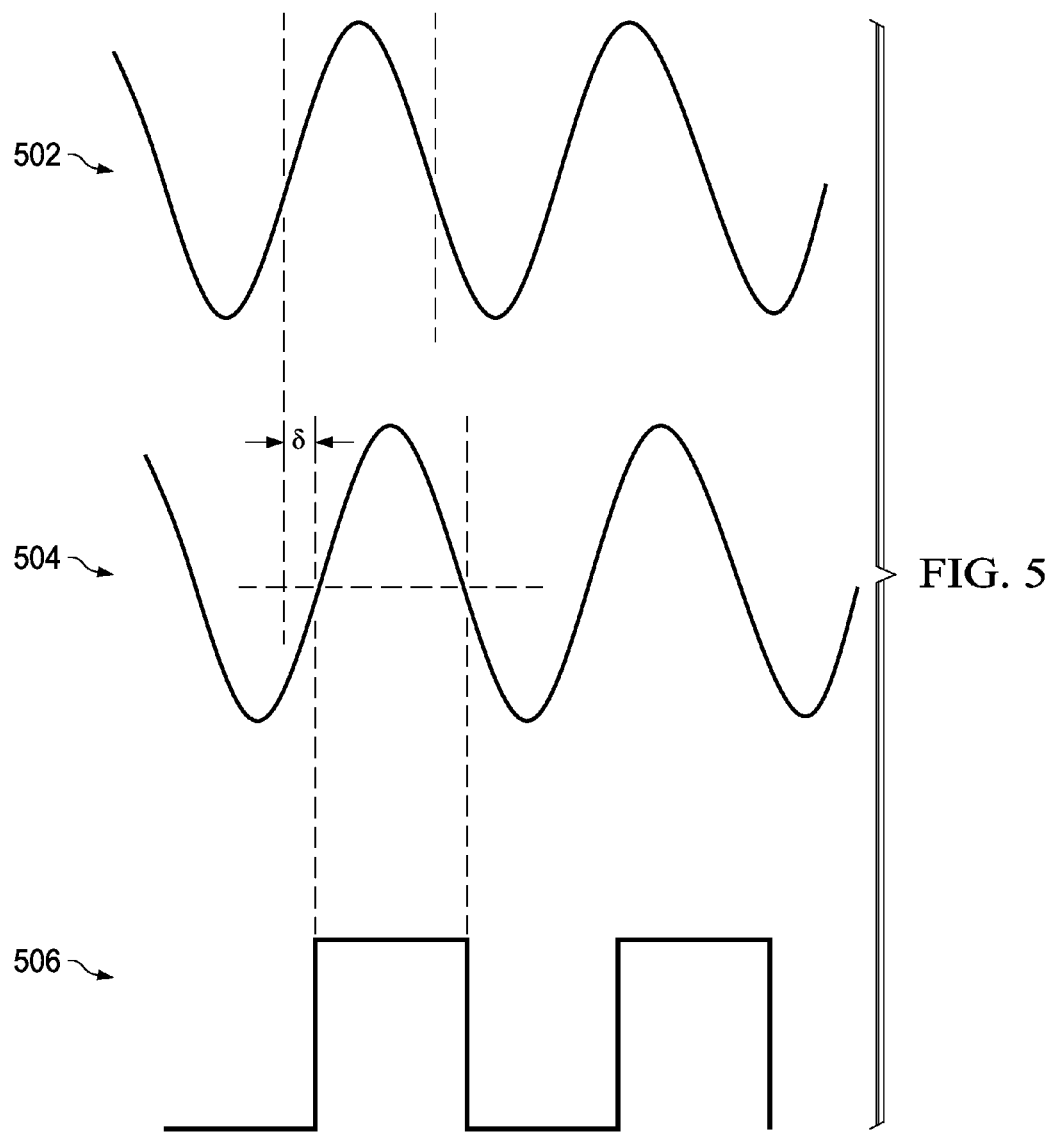
FIG. 5 illustrates waveforms generated in a circuit, according to an embodiment.

FIG. 5 illustrates waveforms generated in a circuit, according to an embodiment. The waveforms are explained in connection with circuit 400 illustrated in FIG. 4. In one example, the waveforms are generated in an impedance measurement circuit. An excitation signal (or an AC signal) generated by an excitation source for example excitation source 410 is illustrated as 502.

The excitation signal 502 is injected in the human body through the pair of excitation electrodes. A voltage difference is created between the first sense terminal S1 414 and the second sense terminal S2 416. The switched resistor network 440 generates an output signal in response to the excitation signal 502 received from the excitation source 410. The output signal is proportional to the voltage difference created between the first sense terminal S1 414 and the second sense terminal S2 416. The sense circuit 420 generates a sense signal in response to the output signal. The sense signal is represented as 504.

A phase shift between the excitation signal 502 and the sense signal 504 is represented as δ. The phase shift δ is introduced because of the phase shifts by the body impedance RBODY 402, and parasitic capacitances of the excitation and sense electrodes. The comparator 460 receives the output signal from the sense circuit 420, and generates a clock signal. The clock signal is represented as 506.

Since, the comparator 460 generates the clock signal 506 from the sense signal 504, the clock signal 506 and the sense signal 504 are in-phase. Also, generating the clock signal 506 from the sense signal 504 eliminates errors due to additional phase shifts in the path of body impedance RBODY 402 with respect to the calibration resistor Rc 432. This leads to accurate measurement of the body impedance RBODY 402.

Figure 6:
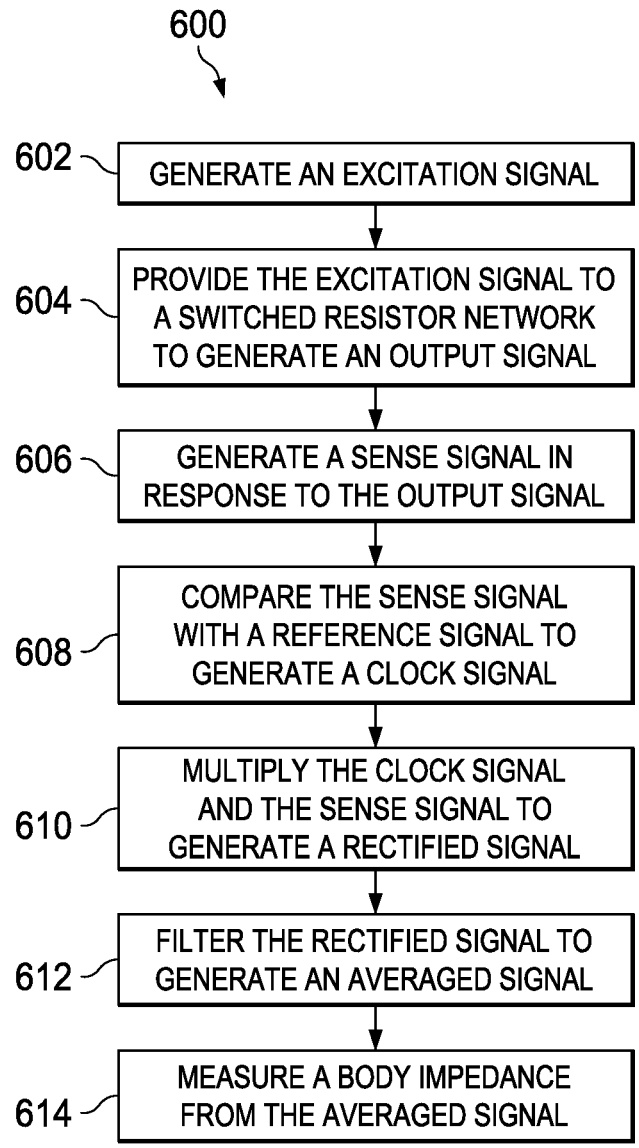
FIG. 6 illustrates a method of impedance measurement, according to an embodiment.

FIG. 6 illustrates a method 600 of impedance measurement, according to an embodiment. At step 602, an excitation signal is generated. In one example, the excitation signal is high frequency AC signal. The AC signal is injected in the human body through a pair of excitation electrodes. A voltage difference is created between a pair of sense electrodes.

In circuit 400 (illustrated in FIG. 4), the excitation source 410 generates an excitation signal. At step 604, a switched resistor network generates an output signal in response to the excitation signal received from the excitation source. The output signal is proportional to the voltage difference created between the pair of sense electrodes.

A sense signal is generated in response to the output signal, at step 606. At step 608, the sense signal is compared with a reference signal to generate a clock signal. In circuit 400, the comparator 460 receives the output signal from the sense circuit 420, and generates a clock signal. The comparator 460 compares the sense signal with the reference signal to generate the clock signal. In one example, the reference signal is generated within the comparator. In another example, the reference signal is provided by the processor 454. In one version, the comparator 460 is a zero crossing detector.

At step 610, the clock signal is multiplied with the sense signal to generate a rectified signal. A time period of the clock signal is equal to a time period of the excitation signal. In one version, a phase of the clock signal is equal to a phase of the excitation signal. Since, the clock signal is generated from the sense signal, the clock signal and the sense signal are in-phase. Also, generating the clock signal from the sense signal eliminates errors due to additional phase shifts in the path of body impedance (for example body impedance RBODY 402) with respect to a calibration resistor. This leads to accurate measurement of an impedance of human body.

At step 612, the rectified signal is filtered to generate an averaged signal, and at step 614, a body impedance is measured from the averaged signal. As illustrated in circuit 400, the LPF 452 filters the rectified signal received from the mixer 450, and generates an averaged signal. The processor 454 measures the body impedance RBODY 402 from the averaged signal. An impedance associated with the human body (for example 102) is represented as a body impedance RBODY.

Figure 7:
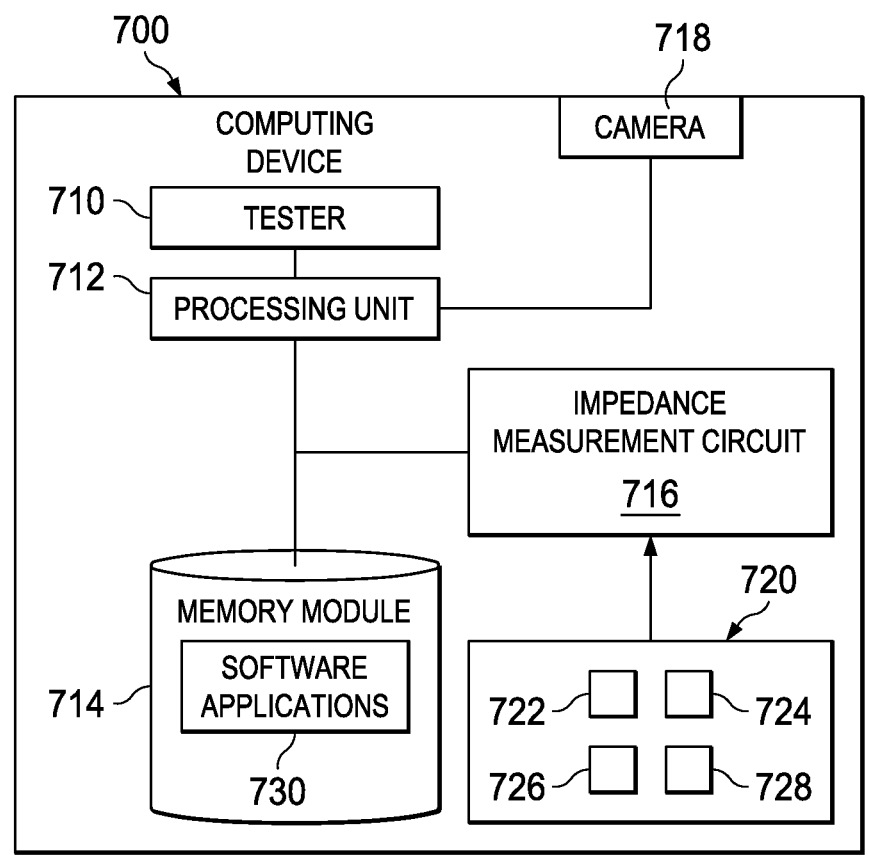
FIG. 7 illustrates a computing device, according to an embodiment.

FIG. 7 illustrates a computing device 700, according to an embodiment. The computing device 700 is, or is incorporated into, a mobile communication device, such as a mobile phone, a personal digital assistant, a transceiver, a personal computer, or any other type of electronic system. The computing device 700 may include one or more additional components known to those skilled in the relevant art and are not discussed here for simplicity of the description.

In some embodiments, the computing device 700 comprises a megacell or a system-on-chip (SoC) which includes a processing unit 712 such as a CPU (Central Processing Unit), a memory module 714 (e.g., random access memory (RAM)) and a tester 710. The processing unit 712 can be, for example, a CISC-type (Complex Instruction Set Computer) CPU, RISC-type CPU (Reduced Instruction Set Computer), or a digital signal processor (DSP).

The memory module 714 (which can be memory such as RAM, flash memory, or disk storage) stores one or more software applications 730 (e.g., embedded applications) that, when executed by the processing unit 712, performs any suitable function associated with the computing device 700. The tester 710 comprises logic that supports testing and debugging of the computing device 700 executing the software applications 730.

For example, the tester 710 can be used to emulate a defective or unavailable component(s) of the computing device 700 to allow verification of how the component(s), were it actually present on the computing device 700, would perform in various situations (e.g., how the component(s) would interact with the software applications 730). In this way, the software applications 730 can be debugged in an environment which resembles post-production operation.

The processing unit 712 typically comprises memory and logic which store information frequently accessed from the memory module 714. A camera 718 is coupled to the processing unit 712. The computing device 700 includes an impedance measurement circuit 716. The impedance measurement circuit 716 is coupled to the processing unit 712 and the memory module 714. The impedance measurement circuit 716 is coupled to an electrode chip 720.

The electrode chip 720 includes a first excitation electrode 722, a second excitation electrode 724, a first sense electrode 726 and a second sense electrode 728. In one version, the electrode chip 720 is integrated in the computing device 700. In another version, the first excitation electrode 722, the second excitation electrode 724, the first sense electrode 726 and the second sense electrode 728 are positioned in the computing device 700 appropriately based on the application of the computing device 700. In yet another version, the electrode chip is separate from the computing device 700, and may communicate with the computing device 700 by a wired/wireless medium. In a different version, the electrode chip 720 includes a plurality of electrodes. The operation of the impedance measurement circuit 716 is similar the operation of the circuit 400 illustrated in FIG. 4.

The first excitation terminal E1 404 in circuit 400 corresponds to the first excitation electrode 722, and the second excitation terminal E2 406 corresponds to the second excitation electrode 724. An impedance associated with the first excitation electrode 722 is represented by the first input electrode impedance RE1 424, and an impedance associated with the second excitation electrode 724 is represented by a second input electrode impedance RE2 426.

The first sense terminal S1 414 corresponds to the first sense electrode 726, and the second sense terminal S2 416 corresponds to the second sense electrode 728. An impedance associated with the first sense electrode 726 is represented as the first output electrode impedance RE3 434, and an impedance associated with the second sense electrode 728 is represented as the second output electrode impedance RE4 436. The impedance measurement circuit 716 includes a calibration resistor similar to the calibration resistor Rc 432.

An excitation signal generated by an excitation source (for example the excitation source 410) has equal magnitudes when the processor measures the body impedance (for example RBODY 402) and the resistance of the calibration resistor Rc 432. In one version, a voltage generated as the excitation signal is equal during measurement of body impedance RBODY 402 and during measurement of the calibration resistor Rc 432. This leads to accurate measurement of an offset associated with the impedance measurement circuit 716.

In addition, the clock signal in the impedance measurement circuit 716 is generated from the sense signal. Thus, the clock signal and the sense signal are in-phase. Also, generating the clock signal from the sense signal eliminates errors due to additional phase shifts in the path of body impedance with respect to the calibration resistor Rc 432. This leads to accurate measurement of the body impedance.

The foregoing description sets forth numerous specific details to convey a thorough understanding of the invention. However, it will be apparent to one skilled in the art that the invention may be practiced without these specific details. Well-known features are sometimes not described in detail in order to avoid obscuring the invention. Other variations and embodiments are possible in light of above teachings, and it is thus intended that the scope of invention not be limited by this Detailed Description, but only by the following Claims.

What is claimed is:

1. A circuit comprising:
   a sense circuit;
   a first electrode;
   a first switch coupled between an excitation source and a calibration resistor;
   the calibration resistor coupled to the first switch and to the electrode; and
   a second switch coupled between the electrode and the sense circuit,
   wherein the sense circuit is configured to close both the first switch and the second switch during measurement of an impedance;
   a third switch, wherein the excitation source is coupled between the first switch and the third switch;
   a fourth switch coupled to the sense circuit;
   a first input electrode impedance coupled to the calibration resistor at a first common node;
   a second input electrode impedance coupled to the third switch at a second terminal, wherein the impedance being measured is coupled between the first input electrode impedance and the second input electrode impedance;
   a first output electrode impedance coupled to a first sense terminal and the first input electrode impedance; and
   a second output electrode impedance coupled to a second sense terminal and the second input electrode impedance.

2. The circuit of claim 1 further comprising:
   a comparator coupled to the sense circuit, and configured to generate a clock signal in response to a sense signal of the sense circuit, wherein the comparator is a zero crossing detector.

3. The circuit of claim 2, the excitation source is configured to generate an excitation signal, and wherein a time period of the clock signal and the excitation signal is equal.

4. The circuit of claim 1 further comprising:
   a fifth switch; and a sixth switch, wherein the fifth and sixth switches are coupled across the calibration resistor, and coupled to the sense circuit.

5. The circuit of claim 1, wherein:
a node common to the first input electrode impedance, the impedance being measured, and the first output electrode impedance is a second common node; and
a node common to the second input electrode impedance, the impedance being measured, and the second output electrode impedance are coupled to form a third common node.

6. The circuit of claim 1, wherein the second switch is coupled between a first sense terminal and the sense circuit; and
the fourth switch is coupled between a second sense terminal and the sense circuit.

7. The circuit of claim 4, wherein the fifth switch is coupled between a first terminal and the sense circuit; and
a sixth switch is coupled between the first common node and the sense circuit.

8. The circuit of claim 1, wherein the sense circuit is further configured to close the third switch and the fourth switch during measurement of an impedance.

9. The circuit of claim 1, wherein the sense circuit is further configured to close the first switch, the second switch, the third switch, and the fourth switch during measurement of a resistance of the calibration resistor.

10. The circuit of claim 3, wherein the excitation signal generated by the excitation source has equal magnitude when the sense circuit measures the impedance and the resistance of the calibration resistor.

11. A circuit comprising:
an excitation source coupled between a first input switch and a second input switch;
a sense circuit coupled to a first set of output switches;
a calibration resistor coupled to the first input switch at a first excitation terminal; and
an impedance network coupled to the calibration resistor, the second input switch and the first set of output switches.

12. The circuit of claim 11 further comprising a second set of output switches coupled across the calibration resistor, and coupled to the sense circuit.

13. The circuit of claim 11 further comprising:
a comparator coupled to the sense circuit, and configured to generate a clock signal in response to a sense signal received from the sense circuit;
a mixer coupled to the sense circuit, and configured to multiply the sense signal and the clock signal to generate a rectified signal;
a low pass filter coupled to the mixer and configured to filter the rectified signal to generate an averaged signal; and
a processor coupled to the low pass filter and configured to measure a body impedance from the averaged signal.

14. The circuit of claim 11, wherein the impedance network comprises:
a first input electrode impedance coupled to the calibration resistor at a first common node;
a second input electrode impedance coupled to the second input switch at a second excitation terminal, wherein the body impedance coupled is between the first input electrode impedance and the second input electrode impedance;
a first output electrode impedance coupled to a first sense terminal; and a second output electrode impedance coupled to a second sense terminal.

15. The circuit of claim 11, wherein the first set of output switches comprises:
a first output switch coupled between the first sense terminal and the sense circuit; and
a second output switch coupled between the second sense terminal and the sense circuit.

16. The circuit of claim 12, wherein the second set of output switches comprises:
a third output switch coupled between the first excitation terminal and the sense circuit; and
a fourth output switch coupled between the first common node and the sense circuit.

17. A method comprising:
closing a first input switch, the first input switch coupled between an excitation source and a calibration resistor, an electrode coupled between the first input switch and the calibration resistor:
closing a second input switch coupled between the electrode and a sense circuit;
measuring an impedance of the electrode when each of the first input switch and the second input switch are being closed,
generating an excitation signal by the excitation source;
providing the excitation signal to a switched resistor network to generate an output signal;
generating a sense signal in response to the output signal;
comparing the sense signal with a reference signal to generate a clock signal;
multiplying the clock signal and the sense signal to generate a rectified signal;
filtering the rectified signal to generate an averaged signal, wherein the impedance is being measured from the averaged signal; and
generating an offset signal to be subtracted from the measured impedance to obtain an impedance having increased accuracy.

18. The method of claim 17, wherein a time period of the clock signal and the excitation signal is equal.

19. The method of claim 17, wherein the switched resistor network comprises:
a first input switch and a second input switch, wherein the excitation source is coupled between the first input switch and the second input switch, the excitation source generates the excitation signal;
a first set of output switches coupled to the sense circuit, the sense circuit generates the sense signal;
the calibration resistor coupled to the first input switch at a first excitation terminal;
an impedance network coupled to the calibration resistor, the second input switch, and the first set of output switches; and
a second set of output switches coupled across the calibration resistor, and coupled to the sense circuit.

20. The method of claim 19, wherein measuring the impedance from the averaged signal further comprises closing the first set of output switches.

21. The method of claim 19 further comprising:
measuring a resistance of the calibration resistor when the first input switch, the second input switch, and the second set of output switches are closed.

22. The method of claim 21, wherein the excitation signal has equal magnitude when measuring the impedance and the resistance of the calibration resistor.

* * * * *